US012702800B2

(12) United States Patent
Ushida et al.

(10) Patent No.: US 12,702,800 B2
(45) Date of Patent: Aug. 11, 2026

(54) GUIDE WIRE

(71) Applicant: ASAHI INTECC CO., LTD., Seto (JP)

(72) Inventors: Keisuke Ushida, Seto (JP); Kenji Yoshida, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 962 days.

(21) Appl. No.: 17/119,583

(22) Filed: Dec. 11, 2020

(65) Prior Publication Data

US 2021/0093840 A1 Apr. 1, 2021

Related U.S. Application Data

(63) Continuation of application No. PCT/JP2018/024865, filed on Jun. 29, 2018.

(51) Int. Cl.
*A61M 25/09* (2006.01)

(52) U.S. Cl.
CPC ... *A61M 25/09* (2013.01); *A61M 2025/09083* (2013.01); *A61M 2025/09133* (2013.01); *A61M 2205/02* (2013.01)

(58) Field of Classification Search
CPC .................... A61M 25/09; A61M 2025/09083
See application file for complete search history.

(56) References Cited

U.S. PATENT DOCUMENTS 5,065,769 A * 11/1991 de Toledo ................ A61B 6/12 604/528
6,001,068 A 12/1999 Uchino et al.
6,602,208 B2 8/2003 Jafari
2004/0039308 A1 2/2004 Murayama et al.
2004/0167443 A1* 8/2004 Shireman ............. A61M 25/09 600/585
2008/0045908 A1* 2/2008 Gould .................. A61M 25/09 604/272

(Continued)

FOREIGN PATENT DOCUMENTS

JP H04-292174 A 10/1992
JP H11-57014 A 3/1999

(Continued)

OTHER PUBLICATIONS

U.S. Appl. No. 17/150,019, filed Jan. 15, 2021 in the name of Yonezawa.

(Continued)

*Primary Examiner* — Jason M Sims
*Assistant Examiner* — Ari S Padda
(74) *Attorney, Agent, or Firm* — Oliff PLC

(57) ABSTRACT

A guide wire includes a first core shaft, a second core shaft, and a covering portion. The second core shaft is made of a material more susceptible to plastic deformation than a material of the first core shaft, and has a proximal end side joined to a distal end side of the first core shaft. The covering portion covers (i) a joint part between the first and second core shafts, and (ii) at least a part of the second core shaft on a distal end side of the joint part. The guide wire includes a first region where the second core shaft on a distal end side of the joint part is covered by the covering portion, and a second region adjacent to the first region, where the joint part is covered by the covering portion. The first region is more susceptible to plastic deformation than the second region.

21 Claims, 14 Drawing Sheets

(56) References Cited

U.S. PATENT DOCUMENTS

2008/0171217 A1 7/2008 Mishima
2008/0183182 A1* 7/2008 Satou .................... A61M 25/09 600/585
2008/0281396 A1 11/2008 Ishida et al.
2011/0015618 A1* 1/2011 Satou .............. A61M 25/09016 604/528
2011/0160703 A1 6/2011 Matsumoto et al.
2011/0160705 A1* 6/2011 Matsumoto ........... A61M 25/09 604/528
2012/0323145 A1* 12/2012 Nagano ................. A61M 25/09 600/585
2015/0005746 A1 1/2015 Sato
2017/0072170 A1 3/2017 Akitomo

FOREIGN PATENT DOCUMENTS

JP 2003-260140 A 9/2003
JP 2004-016359 A 1/2004
JP 2006-508739 A 3/2006
JP 2006-511304 A 4/2006
JP 2006-519069 A 8/2006
JP 2007-503957 A 3/2007
JP 2008-161589 A 7/2008
JP 2008-188670 A 8/2008
JP 4203358 B2 12/2008
JP 2010-503484 A 2/2010
JP 2010-240201 A 10/2010
JP 2011-130976 A 7/2011
JP 2013-544575 A 12/2013
JP 2016-189998 A 11/2016
JP 2017-080153 A 5/2017
JP 2017-513604 A 6/2017
JP 2017-521177 A 8/2017
WO 95/19800 A2 7/1995
WO 1998/018516 A1 5/1998
WO 2004/050162 A1 6/2004
WO 2004/060462 A2 7/2004
WO 2004/075967 A1 9/2004
WO 2005/023357 A2 3/2005
WO 2008/034010 A2 3/2008
WO 2008/139829 A1 11/2008
WO 2009/119386 A1 10/2009
WO 2009/0119387 A1 10/2009
WO 2012/058302 A1 5/2012
WO 2013/136581 A1 9/2013
WO 2015/164250 A1 10/2015
WO 2016/012902 A1 1/2016
WO 2016/047555 A1 3/2016

OTHER PUBLICATIONS

U.S. Appl. No. 17/137,499, filed Dec. 30, 2020 in the name of Yonezawa.
U.S. Appl. No. 17/126,402, filed Dec. 18, 2020 in the name of Ushida et al.

* cited by examiner 1
1p
10
17
16
52
15
20
21
202
61
12
40
11
30
51
O
1d
A
X
Y
Z 52D
1p
15
10D
15
61
20
21
R3
12
40D
11
JP
R2
30
R1
X
51
O
1d
1D
Y
Z

GUIDE WIRE

CROSS REFERENCE TO RELATED APPLICATION

This is a Continuation of Application No. PCT/JP2018/024865 filed Jun. 29, 2018. The disclosure of the prior application is hereby incorporated by reference herein in its entirety.

TECHNICAL FIELD

The disclosed embodiments relate to a guide wire.

BACKGROUND

A guide wire used for inserting a catheter or the like into a blood vessel is known. In such a guide wire, a small curve, or the like is formed on a distal end portion of the guide wire for the purpose of improving blood vessel selectivity to smoothly lead the guide wire to a target site in a blood vessel in some cases. For example, Japanese Unexamined Patent Application Publication Nos. 2007-503957, 2006-511304, and 2006-519069 disclose a guide wire in which shaping of a distal end portion is facilitated by joining a distal end-side shaft (ribbon) made of stainless steel to a distal end of a long shaft (core) made of a nickel-titanium alloy.

However, the guide wires described in Japanese Unexamined Patent Application Publication Nos. 2007-503957, 2006-511304, and 2006-519069 have had problems in that a connection between the long shaft and the distal end-side shaft is not yet easy to shape due to the difference in plasticity between the long shaft formed of a nickel-titanium alloy and the distal end-side shaft made of stainless steel. In addition, the guide wires described in Japanese Unexamined Patent Application Publication Nos. 2007-503957, 2006-511304, and 2006-519069 have had problems in that a part locally susceptible to deformation, e.g. a vicinity of the connection between the long shaft and the distal end-side shaft, or the like, is caused due to the difference in rigidity between the long shaft and the distal end-side shaft.

Incidentally, such problems are not limited to vascular systems, and are common to guide wires to be inserted into each organ in a human body, such as a lymphatic system, a biliary system, a urinary system, a respiratory system, a digestive system, a secretory gland, and a genital organ. In addition, such a problem is not limited to the guide wire including the shaft made of a nickel-titanium alloy and the shaft made of stainless steel, and is common to guide wires formed by joining a plurality of core shafts made of materials having different characteristics.

SUMMARY

The disclosed embodiments have been made to at least partly address the aforementioned problems, and an object of the disclosed embodiments is to provide a guide wire in which a distal end portion can be easily shaped and durability is improved.

The disclosed embodiments can be achieved according to the following aspects.

(1) According to an aspect of the disclosed embodiments, a guide wire is provided. The guide wire includes a first core shaft made of a superelastic material, a second core shaft made of a material more susceptible to plastic deformation than the superelastic material of the first core shaft and having a proximal end side joined to a distal end side of the first core shaft, and a covering portion covering a joint part between the first core shaft and the second core shaft and at least a part of the second core shaft that is on the distal end side of the joint part. From the distal end side toward the proximal end side of the guide wire, a first region where the second core shaft on the distal end side of the joint part is covered by the covering portion, and a second region adjacent to the first region, where the joint part is covered by the covering portion are disposed. The first region is more susceptible to plastic deformation than the second region.

According to this configuration, since the first region more susceptible to plastic deformation than the adjacent second region on the proximal end side is disposed on the distal end side of the guide wire, a distal end portion of the guide wire can be easily shaped. In addition, on both the first region and the second region, a covering portion for covering the joint part between the first and second core shafts and at least a part of the distal end side of the joint part in the second core shaft is disposed. Since this covering portion makes it possible to reduce a rigidity gap between the first and second core shafts having different rigidities, the joint part between the first and second core shafts can be easily shaped, and a part locally susceptible to deformation, such as a vicinity of the joint part, can be protected to prevent breakage of the first and second core shafts, so that durability of the guide wire can be improved.

(2) The guide wire according to the aforementioned aspect further includes a distal end-side fixation portion to fix a distal end portion of the second core shaft. A distal end portion of the covering portion may be fixed by the distal end-side fixation portion. According to this configuration, the distal end portion of the covering portion is fixed by the distal end-side fixation portion for fixing the distal end portion of the second core shaft, i.e. the covering portion is disposed on the second core shaft and also its distal end. Thus, the second core shaft made of a material susceptible to plastic deformation is protected together with its distal end to prevent breakage of the second core shaft, so that durability of the guide wire can be further improved.

(3) In the guide wire according to the aforementioned aspect, a distal end region where the second core shaft is exposed from the covering portion is disposed on the distal end side of the first region, and the distal end region may be more susceptible to plastic deformation than the first region. According to this configuration, since the distal end region more susceptible to plastic deformation than the first region is disposed on the distal end side of the first region, the distal end portion of the guide wire can be more easily shaped. In addition, since the susceptibility of each region in the guide wire to plastic deformation gradually increases from the second region on the proximal end side to the distal end region on the distal end side, it is possible to provide the guide wire in which the distal end side can be easily shaped while preventing breakage of the first and second core shafts on the proximal end side.

(4) In the guide wire according to the aforementioned aspect, the covering portion further covers at least a part of the first core shaft that is on the proximal end side of the joint part, a third region where the first core shaft is covered by the covering portion is disposed on the proximal end side of the second region, and the third region may be less susceptible to plastic deformation than the second region. According to this configuration, the third region less susceptible to plastic deformation than the second region is disposed on the proximal end side of the second region. Thus, the first core shaft on the proximal end side of the joint part between the first and second core shafts can be protected to prevent breakage of the first core shaft, so that durability of the guide wire can be further improved.

(5) In the guide wire according to the aforementioned aspect, a fourth region where the first core shaft is exposed from the covering portion is disposed on the proximal end side of the third region, and the fourth region may be less susceptible to plastic deformation than the third region. According to this configuration, since the fourth region less susceptible to plastic deformation than the third region is disposed on the proximal end side of the third region, breakage of the first core shaft can be prevented, so that durability of the guide wire can be further improved. In addition, since the first core shaft is exposed from the covering portion in the fourth region, a manufacturing cost of the guide wire can be reduced.

(6) In the guide wire according to the aforementioned aspect, a transverse sectional shape of the first core shaft on the joint part may be different from a transverse sectional shape of the second core shaft on the joint part. According to this configuration, since the transverse sectional shape of the first core shaft and the transverse sectional shape of the second core shaft are different from each other on the joint part between the first and second core shafts, a contact face of the first and second core shafts increases between the first and second core shaft adjacent to each other on the joint part, compared to a case of the same shapes. With the guide wire configured in this manner, the joining strength of the first and second core shafts can be improved by filling this contact face as a joining face with a joining agent.

(7) In the guide wire according to the aforementioned aspect, the first core shaft on the joint part may have a substantially rectangular transverse sectional shape, and the second core shaft on the joint part may have a substantially elliptical transverse sectional shape. According to this configuration, the first core shaft has a substantially rectangular transverse sectional shape and the second core shaft has a substantially elliptical transverse sectional shape on the joint part between the first and second core shafts, so that the joining strength of the first and second core shafts can be improved.

(8) In the guide wire according to the aforementioned aspect, a decreasing-diameter portion where an outer diameter of the first core shaft decreases from the proximal end side toward the distal end side is formed on the distal end side of the first core shaft, and the joint part may be disposed on the decreasing-diameter portion. In this configuration, when the decreasing-diameter portion having a decreasing outer diameter is formed on the distal end side of the first core shaft, and the second core shaft is joined to this decreasing-diameter portion (a joint part is formed), the joint includes a large-diameter portion of the first core shaft, so that durability of the guide wire can be improved.

Incidentally, the disclosed embodiments can be achieved in various aspects, e.g. in the form of a core shaft product composed of a plurality of core shafts used in a guide wire, a method for manufacturing a guide wire, or the like.

DETAILED DESCRIPTION OF EMBODIMENTS

First Embodiment

Figure 1:
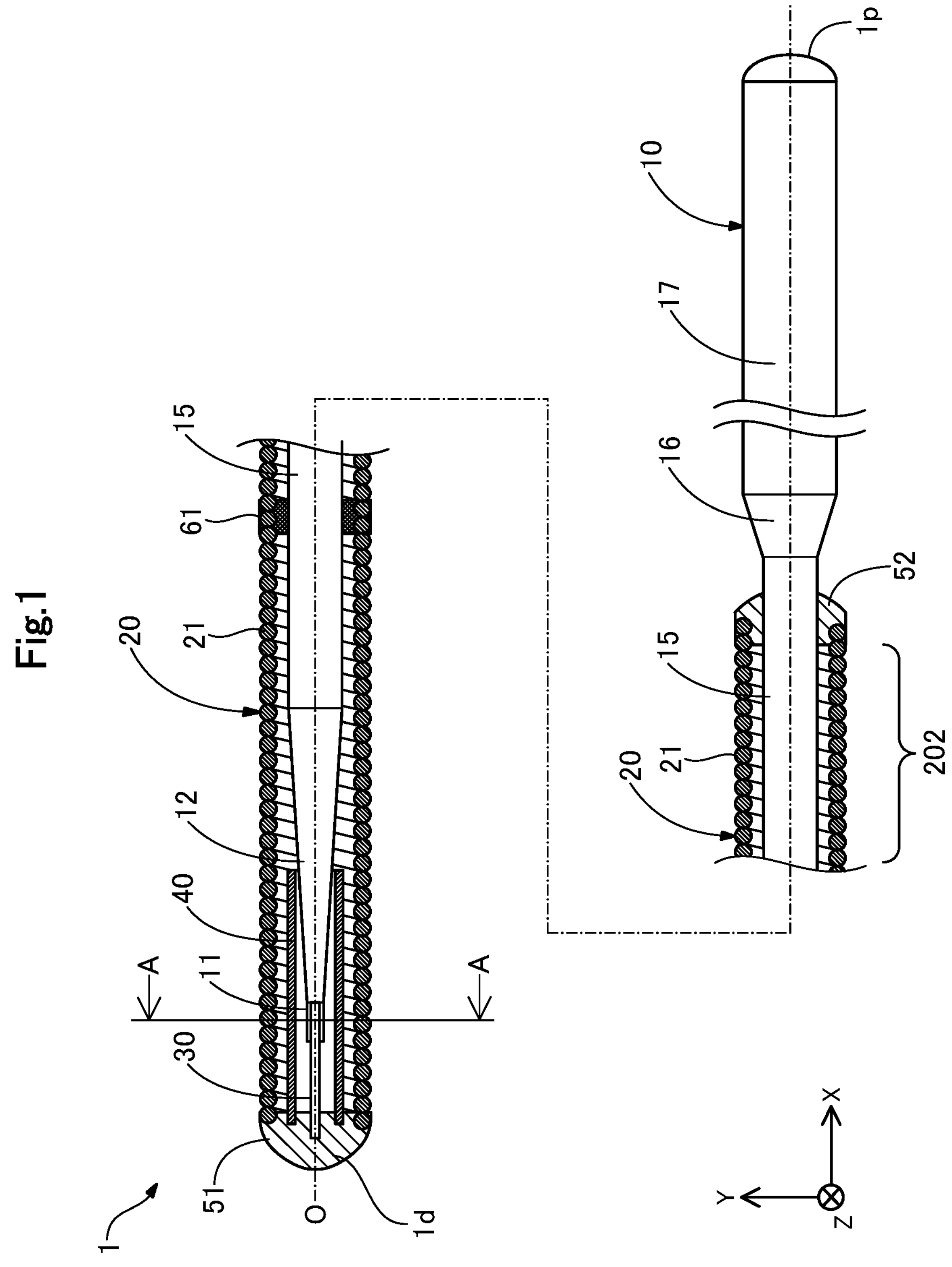
FIG. 1 is a partial sectional view illustrating an overall configuration of a guide wire according to the first embodiment.

FIG. 1 is a partial sectional view illustrating an overall configuration of a guide wire 1 according to the first embodiment. The guide wire 1 is e.g. a medical appliance used for inserting a catheter into a blood vessel, and includes a first core shaft 10, a coil body 20, a second core shaft 30, a covering portion 40, a distal end-side fixation portion 51, a proximal end-side fixation portion 52, and an intermediate fixation portion 61. In FIG. 1, an axis passing through a center of the guide wire 1 is represented by an axis line O (dot and dash line). In the following examples, all of an axis passing through a center of the first core shaft 10 on a proximal end side of a first large-diameter portion 15, an axis passing through a center of the coil body 20, and an axis passing through a center of the covering portion 40 coincide with the axis line O. However, each of the axis passing through the center of the first core shaft 10, the axis passing through the center of the coil body 20, and the axis passing through the center of the covering portion 40 may be inconsistent with the axis line O.

In addition, XYZ axes that are orthogonal to each other are illustrated in FIG. 1. The X axis corresponds to the axis direction of the guide wire 1, the Y axis corresponds to a height direction of the guide wire 1, and the Z axis corresponds to a width direction of the guide wire 1. The left side (−X axis direction) of FIG. 1 is referred to as "distal end side" of the guide wire 1 and each component, and the right side of FIG. 1 (+X axis direction) is referred to as "proximal end side" of guide wire 1 and each component. In addition, regarding the guide wire 1 and each component, the end portion positioned on the distal end side is referred to as "distal end portion" or simply "distal end", the end portion positioned on the proximal end side is referred to as "proximal end portion" or simply "proximal end". In the drawings, the distal end side corresponds to "farther side", and the proximal end side corresponds to "nearer side".

The first core shaft 10 is a long, tapered member with a large diameter on the proximal end side and a small diameter on the distal end side. The first core shaft 10 is made of a superelastic material e.g. a NiTi (nickel-titanium) alloy, or an alloy of NiTi and another metal. The first core shaft 10 has a small-diameter portion 11, a first decreasing-diameter portion 12, a first large-diameter portion 15, a second decreasing-diameter portion 16, and a second large-diameter portion 17, in this order from the distal end side to the proximal end side. An outer diameter and a length of each portion can be arbitrarily determined.

Figure 2:
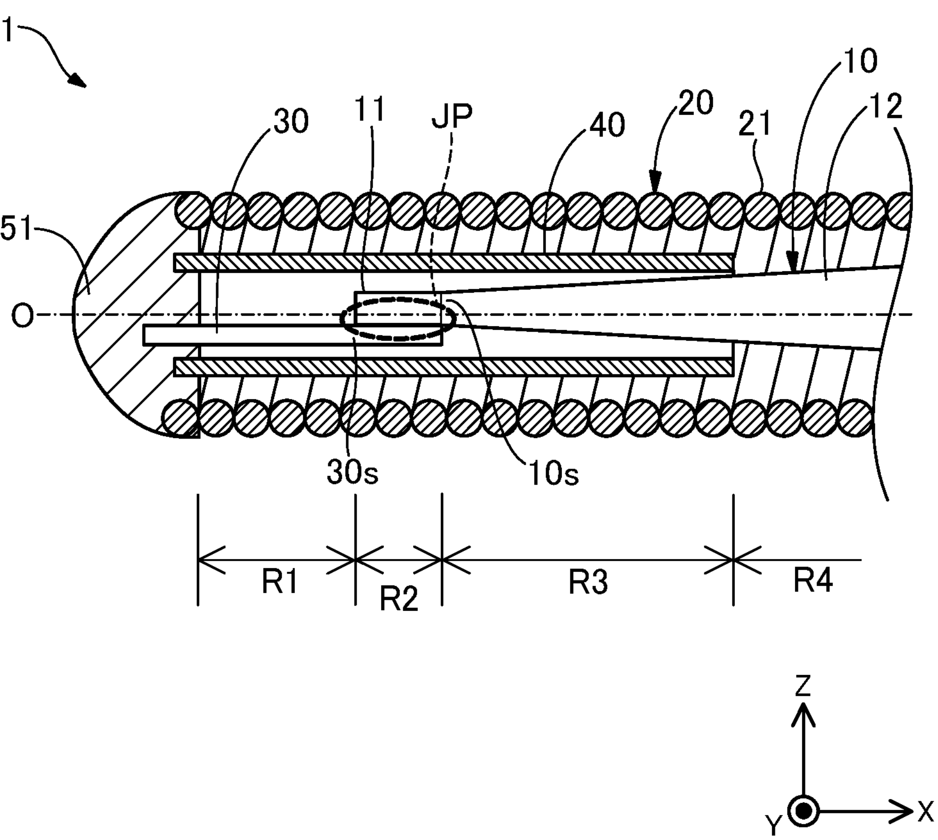
FIG. 2 is a partial sectional view illustrating a distal end side of the guide wire.
Figure 3:
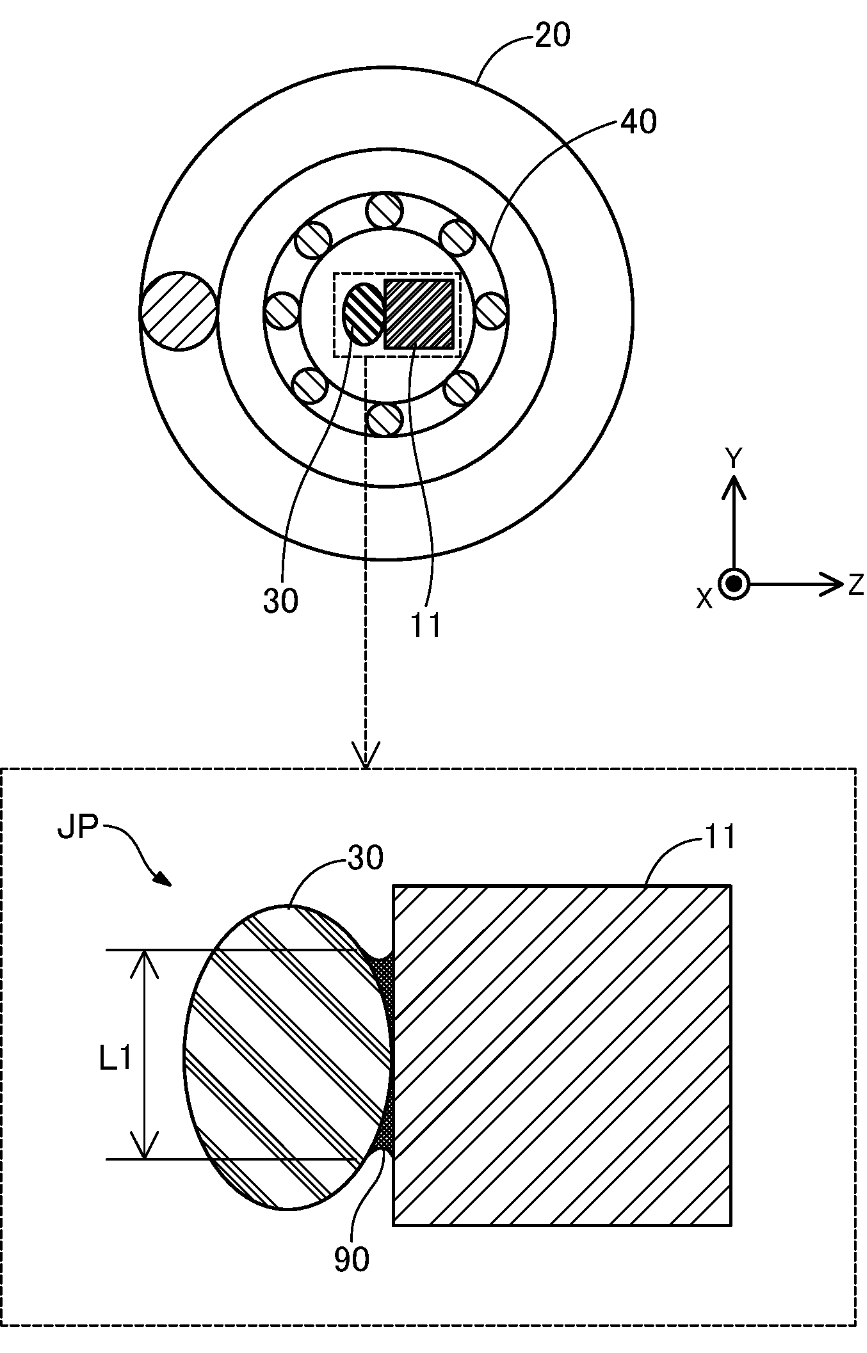
FIG. 3 is a sectional view illustrating the guide wire taken along line A-A (FIG. 1).

FIG. 2 is a partial sectional view illustrating the distal end side of the guide wire 1. FIG. 3 is a sectional view illustrating the guide wire 1 taken along line A-A (FIG. 1). In FIG. 3, the sectional view taken along line A-A is illustrated in the upper part of the drawing, and a partial enlarged view of the vicinity of the joint part JP is illustrated in the lower part of the drawing. The XYZ axes illustrated in FIG. 2 and FIG. 3 correspond to the XYZ axes respectively illustrated in FIG. 1. The same applies to the figures with XYZ axes in the following figures.

The small-diameter portion 11 of the first core shaft 10 is disposed on the distal end side of the first core shaft 10. The small-diameter portion 11 is a portion where the outer diameter of the first core shaft 10 is the smallest, and has a substantially rectangular transverse sectional shape as illustrated in FIG. 3. In FIG. 3, the transverse sectional shape of the small-diameter portion 11 is illustrated as a substantially square shape with substantially same side lengths in the Y-axis direction and the Z-axis direction. Incidentally, the transverse sectional shape of the small-diameter portion 11 may be a substantially rectangular shape with a major side and a minor side, or a substantially rectangular shape with R-chamfered corners or C-chamfered corners. Herein, the "transverse sectional shape" means the cross-sectional shape in a cross section that extends in the YZ plane perpendicular to the X axis.

The first decreasing-diameter portion 12 is disposed between the small-diameter portion 11 and the first large-diameter portion 15. The first decreasing-diameter portion 12 has a substantially truncated cone shape with an outer diameter reducing from the proximal end side to the distal end side. The first large-diameter portion 15 is disposed between the first decreasing-diameter portion 12 and the second decreasing-diameter portion 16. The first large-diameter portion 15 has a substantially cylindrical shape with a certain outer diameter larger than an outer diameter of the small-diameter portion 11. The second decreasing-diameter portion 16 is disposed between the first large-diameter portion 15 and the second large-diameter portion 17. The second decreasing-diameter portion 16 has a substantially truncated cone shape with an outer diameter reducing from the proximal end side to the distal end side. The second large-diameter portion 17 is disposed on the proximal end side of the first core shaft 10. The second large-diameter portion 17 has a substantially cylindrical shape having a certain outer diameter equivalent to the largest outer diameter of the first core shaft 10.

The outer side faces of the small-diameter portion 11, the first decreasing-diameter portion 12, and the first large-diameter portion 15 are covered by the coil body 20 described later. On the other hand, the second decreasing-diameter portion 16 and the second large-diameter portion 17 are not covered by the coil body 20 but are exposed from the coil body 20. The second large-diameter portion 17 is used when an operator grasps the guide wire 1.

The coil body 20 has a substantially cylindrical shape formed by spirally winding a wire 21 around the first core shaft 10 and the second core shaft 30. The wire 21 forming the coil body 20 may be a solid wire composed of one wire, or a twisted wire obtained by twisting a plurality of wires. When the wire 21 is a solid wire, the coil body 20 is configured as a single coil, and when the wire 21 is the twisted wire, the coil body 20 is configured as a hollow twisted wire coil. Alternatively, the coil body 20 may be configured by combining the single coil and the hollow twisted wire coil. The wire diameter of the wire 21 and an average coil diameter in the coil body 20 (average diameter of the outer diameter and the inner diameter of the coil body 20) can be arbitrarily determined.

The wire 21 can be made of, for example, a stainless steel alloy such as SUS304 and SUS316, a superelastic alloy such as a NiTi alloy, a piano wire, a radiolucent alloy such as nickel-chromium alloy and cobalt alloy, gold, platinum, tungsten, or a radiopaque alloy such as an alloy including the aforementioned elements (e.g. platinum-nickel alloy). Incidentally, the wire 21 may be made of a known material other than the aforementioned materials.

The second core shaft 30 is a long member having a certain outer diameter from the proximal end side to the distal end side, and has a substantially elliptical transverse sectional shape with a major axis and a minor axis as illustrated in FIG. 3. The second core shaft 30 is adjacent to the small-diameter portion 11 of the first core shaft 10 such that the major axis is oriented in the Y axis direction and the minor axis is oriented in the Z axis direction. The second core shaft 30 is made of a material that is more susceptible to plastic deformation than the first core shaft 10, e.g. a stainless steel alloy such as SUS304 and SUS316. The second core shaft 30 is also referred to as "ribbon". Incidentally, the second core shaft 30 may be configured such that only a part of the proximal end side corresponding to the joint part JP has a substantially elliptical transverse sectional shape illustrated in FIG. 3, and a part of the distal end side of the joint part JP has a transverse sectional shape different from the substantially elliptical shape (e.g. a substantially circular shape). In addition, the second core shaft 30 may be oriented in a different direction from FIG. 3, e.g. the minor axis is oriented in the Y axis direction, and the major axis is oriented in the Z axis direction.

As illustrated in FIG. 2, the proximal end side of the second core shaft 30 is joined to the small-diameter portion 11 on the distal end side of the first core shaft 10. This joining can be performed in such a way that a gap between the first core shaft 10 (small-diameter portion 11) and the second core shaft 30 that are adjacent to each other is filled with a joining agent 90 and the joining agent 90 is hardened as illustrated in FIG. 3. As the joining agent 90, e.g. a metal solder such as silver solder, gold solder, zinc, Sn—Ag alloy, and Au—Sn alloy, or an adhesive such as epoxy adhesive can be used. In FIG. 2 and FIG. 3, the joint part between the first core shaft 10 and the second core shaft 30 is referred to as "joint part JP". The distal end side of the second core shaft 30 is fixed by the distal end-side fixation portion 51 described later.

In the example of FIG. 2, the second core shaft 30 is joined to the first core shaft 10 such that a position of the proximal end portion of the second core shaft 30 and a position of the proximal end portion of the small-diameter portion 11 coincide with each other in the axis line O (X axis) direction. However, the position of the proximal end portion of the second core shaft 30 and the position of the proximal end portion of the small-diameter portion 11 in the axis line O direction may be different from each other. For example, the proximal end portion of the second core shaft

30 may be positioned on the −X axis direction side of the proximal end portion of the small-diameter portion 11.

Figure 4:
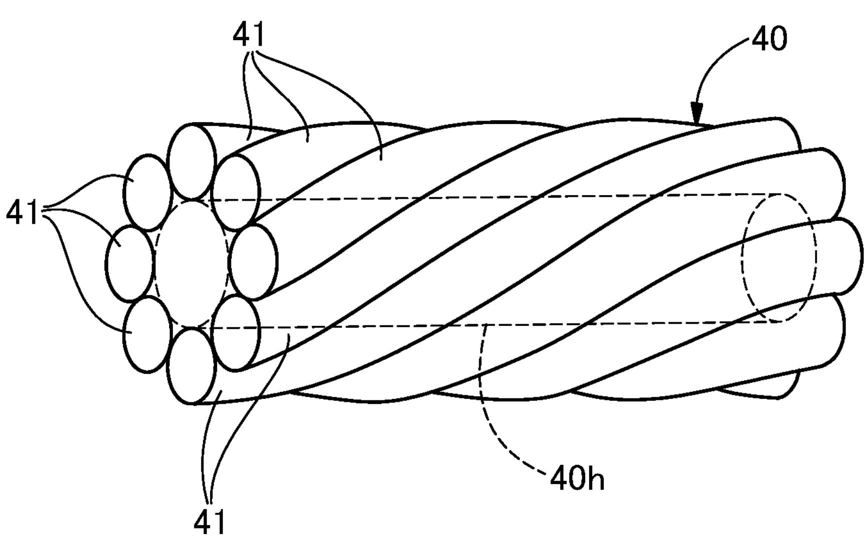
FIG. 4 is a perspective view illustrating a schematic configuration of a covering portion.

FIG. 4 is a perspective view illustrating a schematic configuration of the covering portion 40. The covering portion 40 according to the first embodiment is a multi-thread coil obtained by winding eight wires 41, and is less susceptible to plastic deformation than the second core shaft 30 and more susceptible to plastic deformation than the first core shaft 10. The covering portion 40 can be formed e.g. in such a way that the eight wires 41 are tightly twisted around a cored bar so as to be in contact with each other, then a residual stress is removed using a known heat treatment method, and the cored bar is drawn out. The covering portion 40 formed in this way is a multi-thread coil having an inner cavity 40*h* (FIG. 4: dashed line) as illustrated in FIG. 4. A material of the wire 41 may be the same as or different from that of the wire 21.

Incidentally, for the covering portion 40, any configuration can be adopted as long as the covering portion 40 is configured to be less susceptible to plastic deformation than the second core shaft 30 and more susceptible to plastic deformation than the first core shaft 10. For example, a number of the wires constituting the covering portion 40 is not limited to eight, and can be arbitrarily determined. The covering portion 40 is not limited to the multi-thread coil, and may be a single-thread coil formed of one wire, or a tubular member made of a resin or a metal and formed into a tube shape, or alternatively may be coated with a hydrophobic resin material, a hydrophilic resin material, or a mixture thereof.

As illustrated in FIG. 2 and FIG. 3, inside the coil body 20, the covering portion 40 is arranged so as to cover a part of the distal end side of the first core shaft 10, the joint part JP, and the second core shaft 30. In other words, the first core shaft 10 and second core shaft 30 joined to each other pass through the inner cavity 40*h* of the covering portion 40 and extend in the axis line O direction. The distal end portion of the covering portion 40 is fixed by the distal end-side fixation portion 51 described later. The proximal end portion of the covering portion 40 is disposed in the vicinity of the center of the first decreasing-diameter portion 12 of the first core shaft 10 (FIG. 2). Incidentally, the proximal end portion of the covering portion 40 may or may not be fixed to the first decreasing-diameter portion 12 of the first core shaft 10 using any joining agent.

The distal end-side fixation portion 51 is disposed on the distal end portion of the guide wire 1 and integrally holds the distal end portion of the second core shaft 30, the distal end portion of the coil body 20, and the distal end portion of the covering portion 40. The distal end-side fixation portion 51 can be formed from any joining agent, e.g. a metal solder such as silver solder, gold solder, zinc, Sn—Ag alloy, and Au—Sn alloy, or an adhesive such as epoxy adhesive. The proximal end-side fixation portion 52 is disposed on the proximal end portion of the first large-diameter portion 15 of the first core shaft 10 and integrally holds the first core shaft 10 and the proximal end portion of the coil body 20. The proximal end-side fixation portion 52 can be formed from any joining agent in the same manner as for the distal end-side fixation portion 51. For the proximal end-side fixation portion 52 and the distal end-side fixation portion 51, the same joining agent or different joining agents may be used.

The intermediate fixation portion 61 integrally holds the coil body 20 and the first core shaft 10 in the vicinity of the intermediate portion of the coil body 20 in the axis line O direction. The intermediate fixation portion 61 can be formed from any joining agent in the same manner as for the distal end-side fixation portion 51. For the intermediate fixation portion 61 and the distal end-side fixation portion 51, the same joining agent or different joining agents may be used. Although one intermediate fixation portion 61 has been described as an example in FIG. 1, a plurality of intermediate fixation portions 61 may be disposed on the guide wire 1.

Herein, as illustrated in FIG. 2, a part where the joint part JP between the first core shaft 10 and the second core shaft 30 is covered by the covering portion 40 is referred to as "second region R2", a part where the second core shaft 30 on the distal end side of the joint part JP is covered by the covering portion 40 is referred to as the "first region R1", a part where the first core shaft 10 (first decreasing-diameter portion 12) on the proximal end side of the joint part JP is covered by the covering portion 40 is referred to as "third region R3", and a part where the first core shaft 10 is exposed from the covering portion 40 is referred to as "fourth region R4". That means, in the first embodiment, the first region R1, the second region R2, the third region R3, and the fourth region R4 are disposed in this order from the distal end side to the proximal end side of the guide wire 1. In other words, the first region R1 is positioned on the most distal side, the second region R2 is positioned on the proximal end side of the first region R1, the third region R3 is positioned on the proximal end side of the second region R2, and the fourth region R4 is positioned on the proximal end side of the third region R3 (most proximal end side).

As described above, the first core shaft 10 is made of a superelastic material, and the second core shaft 30 is made of a material more susceptible to plastic deformation than of the first core shaft 10. The covering portion 40 is configured to be less susceptible to plastic deformation than the second core shaft 30 and more susceptible to plastic deformation than the first core shaft 10. Thus, a relationship of each member on the susceptibility to plastic deformation is expressed as "the second core shaft 30>the covering portion 40>the first core shaft 10". In addition, as illustrated in FIG. 1, the diameter of the first core shaft 10 (first decreasing-diameter portion 12) exposed from the covering portion 40 increases from the distal end side to the proximal end side, and becomes substantially the same as the outer diameter of the covering portion 40 in the vicinity of the boundary with the first large-diameter portion 15. As a result, the aforementioned susceptibility of each region in the guide wire 1 to plastic deformation gradually decreases from the first region R1 to the fourth region R4 in the order of (the first region R1>the second region R2>the third region R3>the fourth region R4).

As described above, in the guide wire 1 according to the first embodiment, the first region R1 more susceptible to plastic deformation than the second region R2 adjacent to the proximal end side (+X axis direction) of the first region R1 is disposed on the distal end side (−X axis direction) of the guide wire 1 (FIG. 2). Thus, the distal end portion of the guide wire 1 can be easily shaped by squeezing the distal end portion of the guide wire 1 with e.g. fingertips or a tip of a syringe needle. In addition, a covering portion 40 for covering the joint part JP between the first core shaft 10 (small-diameter portion 11) and the second core shaft 30, and at least a part of the second core shaft 30 on the distal end side of the joint part JP is disposed in both the first region R1 and the second region R2 (FIG. 2: first region R1 and second region R2). Owing to this covering portion 40, a rigidity gap between the first and second core shafts 10 and 30 having different rigidities can be reduced, and therefore the joint part JP of the first and second core shafts 10 and 30 can be more easily shaped compared to a configuration without the covering portion 40. Furthermore, reduction in the rigidity gap between the first and second core shafts 10 and 30 in the covering portion 40 makes it possible to protect a part locally susceptible to deformation in the vicinity of the joint part JP, e.g. a part 30*s* of the second core shaft on the distal end side of the joint part JP (FIG. 2), a part 10*s* of the first core shaft 10 on the proximal end side of the joint part JP (FIG. 2), or the like, to prevent breakage of the first and second core shafts 10 and 30, so that durability of the guide wire 1 can be prevented.

Additionally, in the guide wire 1 according to the first embodiment, the distal end portion of the covering portion 40 is fixed by the distal end-side fixation portion 51 for fixing the distal end portion of the second core shaft 30 (FIGS. 1 and 2). That means, in the guide wire 1 according to the first embodiment, the covering portion 40 covers the second core shaft 30 and is fixed to the distal end of the guide wire. In such a way, the second core shaft 30 made of a material susceptible to plastic deformation can be protected to prevent breakage of the second core shaft 30 accompanying shaping and use, so that durability of the guide wire 1 can be further improved.

Furthermore, in the guide wire 1 according to the first embodiment, the third region R3 less susceptible to plastic deformation than the second region R2 is disposed on the proximal end side of the second region R2 (FIG. 2: third region R3). Thereby, the first core shaft 10 positioned on the proximal end side of the joint part JP between the first and second core shafts 10 and 30 can be protected to prevent breakage of the first core shaft 10 accompanying shaping and use, so that durability of the guide wire 1 can be further improved. Furthermore, the fourth region R4 less susceptible to plastic deformation than the third region R3 is disposed on the proximal end side of the third region R3 (FIG. 2: the fourth region R4). Thereby, breakage of the first core shaft 10 can be further improved, so that durability of the guide wire 1 can be further improved. In addition, in the fourth region R4, the first core shaft 10 is exposed from the covering portion 40. Thus, a manufacturing cost of the guide wire 1 can be reduced e.g. compared to a configuration that the covering portion 40 is formed on the coil body 20 and also its proximal end portion.

Furthermore, in the guide wire 1 according to the first embodiment, a transverse sectional shape of the first core shaft 10 (FIG. 3: small-diameter portion 11) on the joint part JP between the first and second core shafts 10 and 30 is a substantially rectangular shape, a transverse sectional shape of the second core shaft 30 (FIG. 3: second core shaft 30) is a substantially elliptical shape, and therefore the shapes of them are different. Thereby, as illustrated in FIG. 3, a contact face between the first and second core shafts 10 and 30 adjacent to each other on the joint part JP increases compared to a case that the small-diameter portion 11 and the second core shaft 30 both have a circular or elliptical transverse sectional shape, for example. According to the guide wire 1 having this configuration, a joining strength between the first and second core shafts 10 and 30 can be improved by filling this contact face as a joining face L1 (FIG. 3) with the joining agent 90.

Second Embodiment

Figure 5:
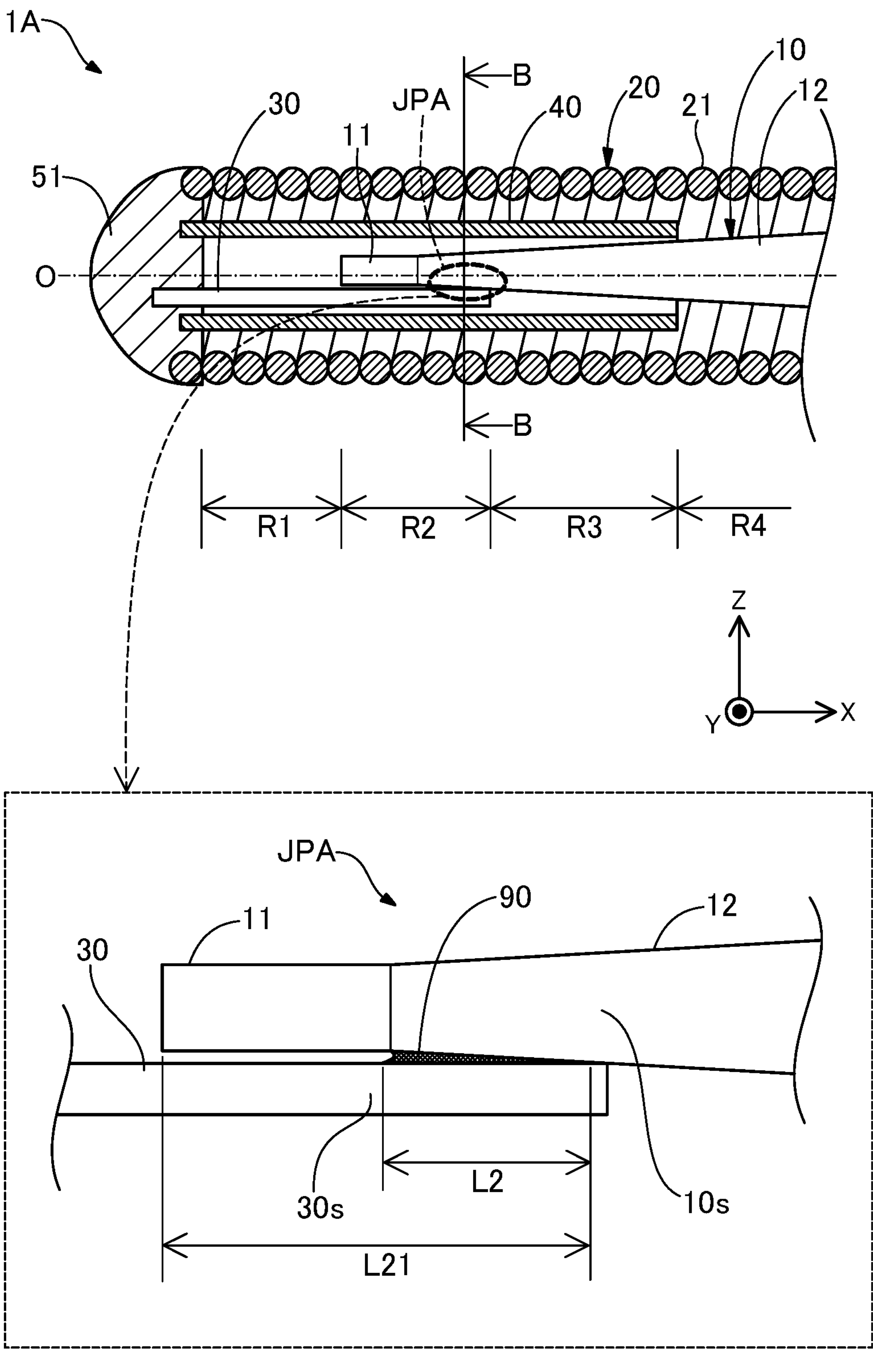
FIG. 5 is a partial sectional view illustrating a distal end side of a guide wire according to the second embodiment.
Figure 6:
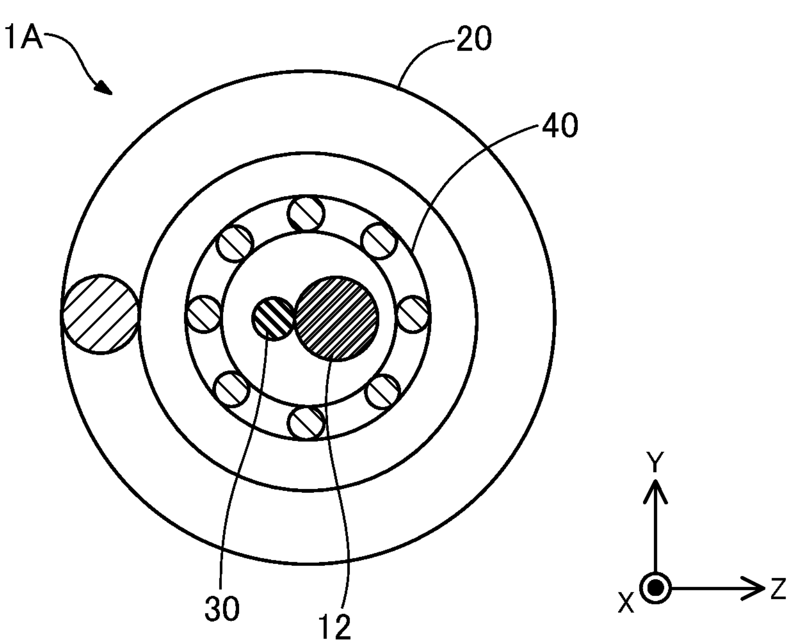
FIG. 6 is a sectional view illustrating the guide wire according to the second embodiment taken along line B-B (FIG. 5).

FIG. 5 is a partial sectional view illustrating a distal end side of a guide wire 1A according to the second embodiment. FIG. 6 is a sectional view illustrating the guide wire 1A according to the second embodiment taken along line B-B (FIG. 5). In FIG. 5, a partial enlarged view of the distal end side of the guide wire 1A is illustrated in the upper part of the drawing, and a partial enlarged view of a vicinity of a joint part JPA is illustrated in the lower part of the drawing. In the guide wire 1A according to the second embodiment, the joint part between the first and second core shafts 10 and 30 is disposed between the first decreasing-diameter portion 12 of the first core shaft 10 and the proximal end portion of the second core shaft 30. The first decreasing-diameter portion 12 gradually decreases in outer diameter from the proximal end side to the distal end side (FIG. 5, lower column), and has a substantially circle transverse sectional shape (FIG. 6). As illustrated in the lower part of FIG. 5, the joint part JPA can be formed by filling the gap between the first decreasing-diameter portion 12 and the second core shaft 30 adjacent to each other with the joining agent 90 and hardening the joining agent 90. For the joining agent 90, the metal solder or the adhesive described as examples in the first embodiment can be used. The joining agent 90 according to the second embodiment may be the same as or different from that in the first embodiment.

In the example on the lower part of FIG. 5, the gap between the small-diameter portion 11 of the first core shaft 10 and the second core shaft 30 is a void without the joining agent 90. However, the void between the small-diameter portion 11 and the second core shaft 30 may be eliminated by filling this gap with the joining agent 90 and hardening the joining agent 90. As described above, in the second embodiment, the joint part JPA includes a part where the small-diameter portion 11 and the second core shaft 30 are adjacent to each other, and the second region R2 includes a part where the small-diameter portion 11 and the second core shaft 30 are adjacent to each other (FIG. 5, upper column: second region R2).

As described above, also in the guide wire 1A according to the second embodiment, the same effect as in the first embodiment described above can be accomplished. Furthermore, in the guide wire 1A according to the second embodiment, the first decreasing-diameter portion 12 having a decreasing outer diameter is formed on the distal end side of the first core shaft 10, and the joint part JPA to which the second core shaft 30 is joined is disposed on this first decreasing-diameter portion 12. Thus, as illustrated in the lower part of FIG. 5, even if the first and second core shafts 10 and 30 adjacent to each other on the joint part JPA have the same transverse sectional shape (FIG. 6), the durability of the guide wire 1A can be improved because the joint part JPA has a joint on the large-diameter part of the first core shaft 10.

Third Embodiment

Figure 7:
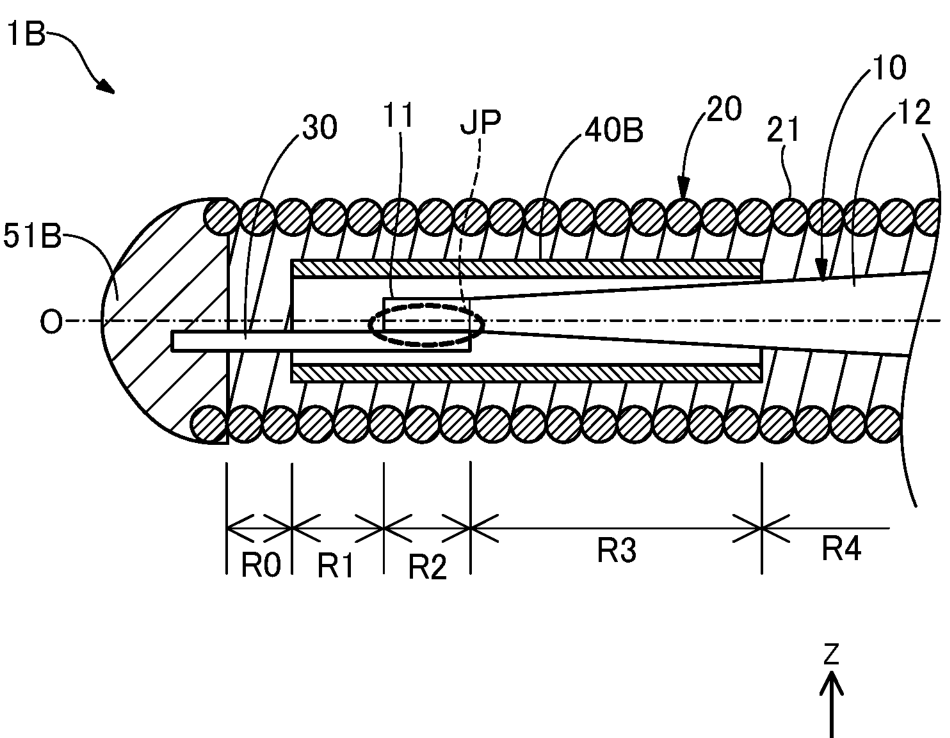
FIG. 7 is a partial sectional view illustrating a distal end side of a guide wire according to the third embodiment.

FIG. 7 is a partial sectional view illustrating a distal end side of a guide wire 1B according to the third embodiment. In the guide wire 1B according to the third embodiment, a distal end region R0 is disposed on the distal end side of the first region R1. In the distal end region R0, the second core shaft 30 is not covered by a covering portion 40B but is exposed from the covering portion 40B. Specifically, the covering portion 40B according to the third embodiment has a length in the axis line O direction (X-axis direction) shorter than the length of the covering portion 40 according to the first embodiment, and is arranged so as to cover not the whole second core shaft 30 but a part on the proximal end side of the second core shaft 30. The proximal end portion of the covering portion 40B is fixed to the first decreasing-diameter portion 12 of the first core shaft 10 using any joining agent. The distal end portion of the covering portion 40B is not fixed to the distal end-side fixation portion 51B and opens in the example in FIG. 7. Incidentally, a distal end portion of the covering portion 40B may be fixed to the second core shaft 30 using any joining agent.

In the third embodiment as described above, the distal end region R0, the first region R1, the second region R2, the third region R3, and the fourth region R4 are disposed in this order from the distal end side to the proximal end side of the guide wire 1B. As described above, a relationship of each member on the susceptibility to plastic deformation is expressed as (the second core shaft 30>the covering portion 40B,>the first core shaft 10). Thus, the distal end region R0 not covered by the covering portion 40B is more susceptible to plastic deformation than the first region R1 covered by the covering portion 40B. That means the susceptibility of each region in the guide wire 1B to plastic deformation gradually decreases from the distal end region R0 to the fourth region R4 in the order of (the distal end region R0>the first region R1>the second region R2>the third region R3>the fourth region R4).

As described above, also in the guide wire 1B according to the third embodiment, the same effect as in the aforementioned first embodiment can be accomplished. Furthermore, in the guide wire 1B according to the third embodiment, the distal end region R0 more susceptible to plastic deformation than the first region R1 is disposed on the distal end side of the first region. This makes it possible to further facilitate shaping of the distal end portion of the guide wire 1B. In addition, since the susceptibility of each region in the guide wire 1B to plastic deformation gradually increases from the fourth region R4 on the proximal end side to the distal end region R0 on the distal end side, it is possible to provide the guide wire 1B in which the distal end side is more easily shaped while preventing breakage of the first and second core shafts 10 and 30 on the proximal end side.

Fourth Embodiment

Figure 8:
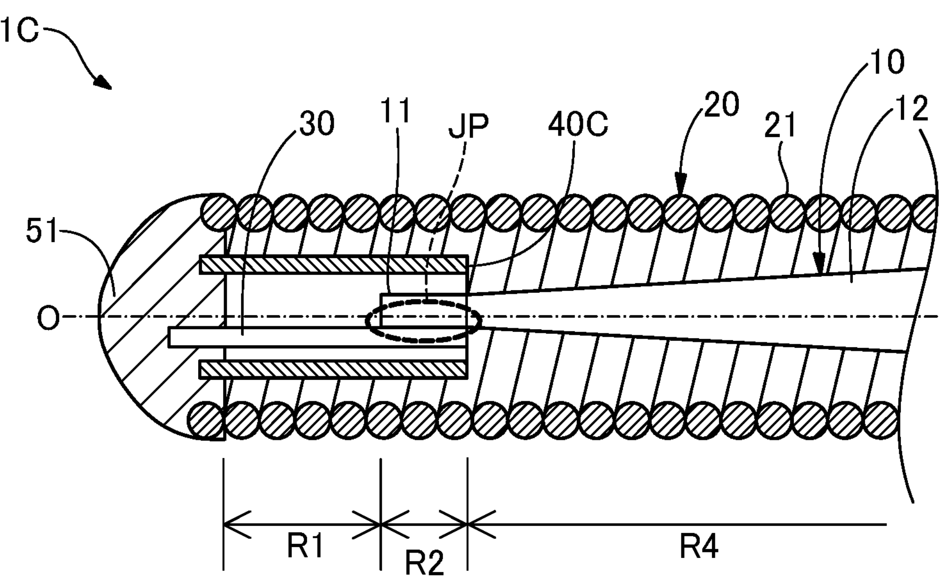
FIG. 8 is a partial sectional view illustrating a distal end side of a guide wire according to the fourth embodiment.
Figure 8:
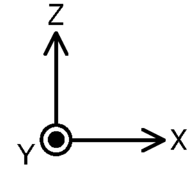

FIG. 8 is a partial sectional view illustrating the distal end side of the guide wire 1C according to the fourth embodiment. In the guide wire 1C according to the fourth embodiment, the third region R3 is not formed. Specifically, the covering portion 40C according to the fourth embodiment has a length in the axis line O direction (X-axis direction) shorter than of the covering portion 40 according to the first embodiment and does not cover the first core shaft 10 (first decreasing-diameter portion 12) on the proximal end side of the joint part JP between the first and second core shafts 10 and 30. In other words, the first core shaft 10 (first decreasing-diameter portion 12) on the proximal end side of the joint part JP is not covered by the covering portion 40C but is exposed. Incidentally, a proximal end portion of the covering portion 40C may be fixed to at least one end of the small-diameter portion 11 of the first core shaft 10 and the second core shaft 30 using any joining agent.

In the fourth embodiment as described above, the first region R1, the second region R2, and the fourth region R4 are disposed in this order from the distal end side to the proximal end side of the guide wire 1C. The susceptibility of each region to plastic deformation gradually decreases from the first region R1 to the fourth region R4, expressed as (the first region R1>the second region R2>the fourth region R4). Thus, the guide wire 1C according to the fourth embodiment accomplishes the same effect as in the first embodiment.

Fifth Embodiment

Figure 9:
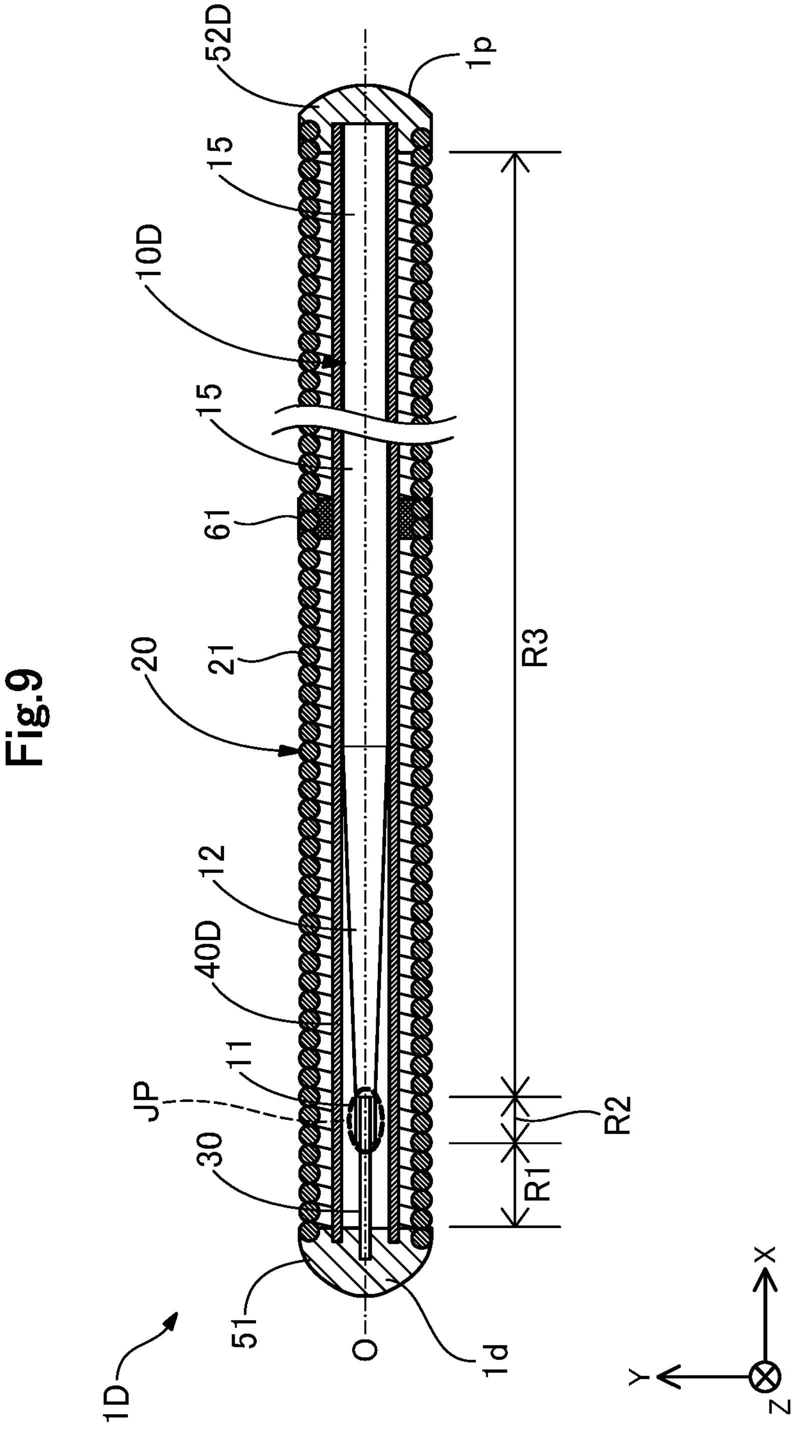
FIG. 9 is a partial sectional view illustrating an overall configuration of a guide wire according to the fifth embodiment.

FIG. 9 is a partial sectional view illustrating an overall configuration of a guide wire 1D according to the fifth embodiment. In the guide wire 1D according to the fifth embodiment, the fourth region R4 is not formed. Specifically, a first core shaft 10D according to the fifth embodiment does not include the second decreasing-diameter portion 16 and the second large-diameter portion 17. In addition, a covering portion 40D has a length in the axis line O direction (X-axis direction) longer than of the covering portion 40 according to the first embodiment, and is arranged so as to cover the whole first core shaft 10D positioned inside the coil body 20. A distal end portion of the covering portion 40D is fixed by the distal end-side fixation portion 51 in the same manner as in the first embodiment. In addition, a proximal end portion of the covering portion 40D is fixed together with the coil body 20 and a proximal end portion of the first core shaft 10D by the proximal end-side fixation portion 52D.

In the fifth embodiment as described above, the first region R1, the second region R2, and the third region R3 are disposed in this order from the distal end side to the proximal end side of the guide wire 1D. The susceptibility of each region to plastic deformation gradually decreases from the first region R1 to the third region R3 in the order of (the first region R1>the second region R2>the third region R3). Thus, the guide wire 1D according to the fifth embodiment accomplishes the same effect as in the first embodiment.

Sixth Embodiment

Figure 10:
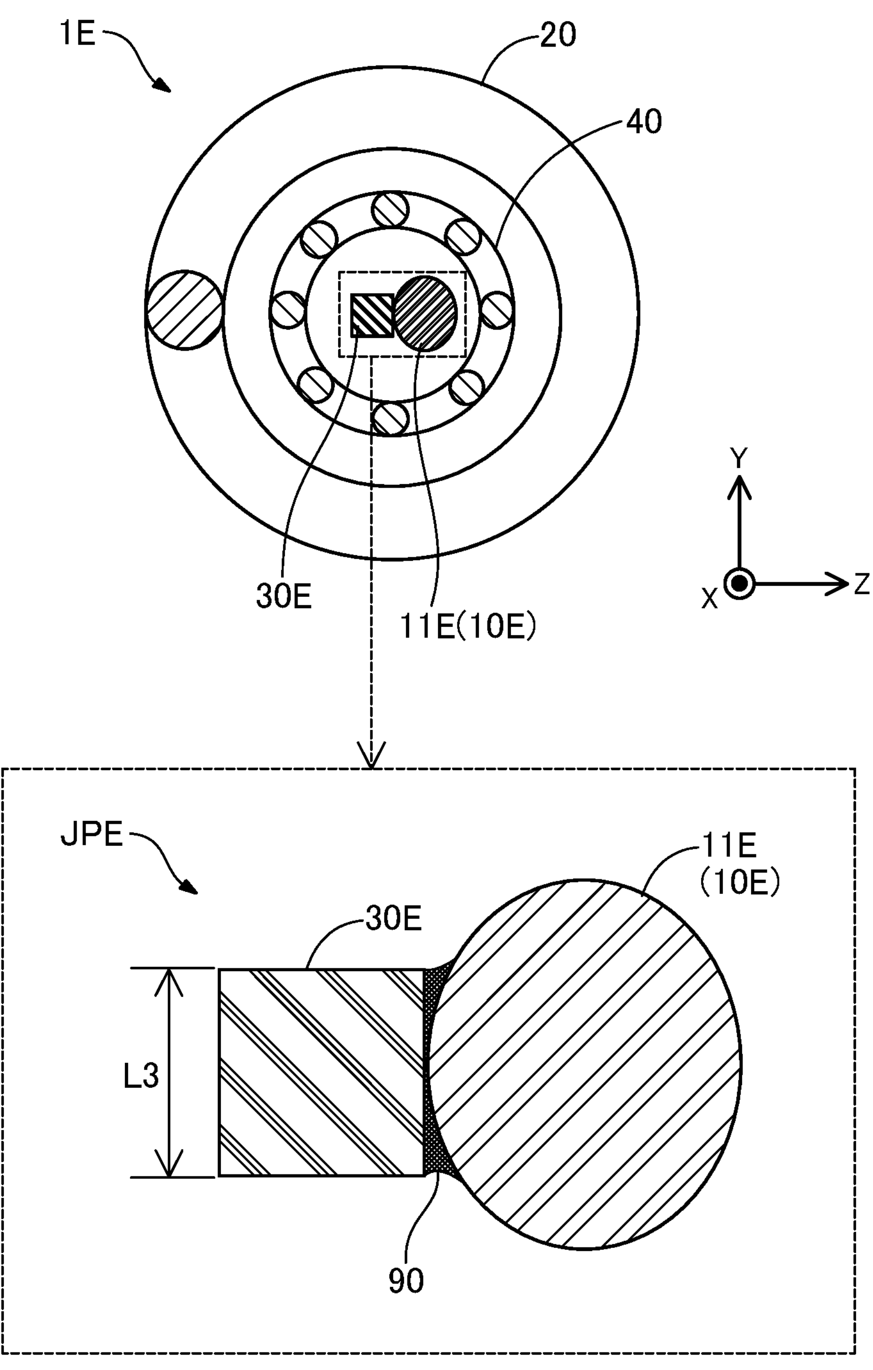
FIG. 10 is a sectional view illustrating a guide wire according to the sixth embodiment taken along line A-A (FIG. 1).

FIG. 10 is a sectional view illustrating a guide wire 1E according to the sixth embodiment taken along line A-A (FIG. 1). In FIG. 10, the sectional view taken along line A-A is illustrated in the upper part of the drawing, and a partial enlarged view of the vicinity of a joint part JPE is illustrated in the lower part of the drawing. In the guide wire 1E according to the sixth embodiment, a first core shaft 10E (small-diameter portion 11E) corresponding to the joint part JPE has a substantially elliptical transverse sectional shape, and a second core shaft 30E corresponding to the joint part JPE has a substantially rectangular transverse sectional shape. The joint part JPA according to the sixth embodiment is formed by filling a gap between the small-diameter portion 11E and a proximal end portion of the second core shaft 30E adjacent to each other with the joining agent 90. For the joining agent 90, the metal solder or the adhesive described as examples in the first embodiment can be used. The joining agent 90 according to the sixth embodiment may be the same as or different from that in the first embodiment.

Also in the sixth embodiment as described above, the transverse sectional shape of the first core shaft 10E (FIG. 10: small-diameter portion 11E) and the transverse sectional shape of the second core shaft 30E (FIG. 10: second core shaft 30E) are different from each other on the joint part JPE, and therefore the same effect as the aforementioned effect in the first embodiment can be accomplished by treating a contact face between the first and second core shafts 10E and 30E adjacent to each other on the joint part JPE as a joining face L3 (FIG. 10). Incidentally, the transverse sectional shape of the first core shaft 10E and the transverse sectional shape of the second core shaft 30E on the joint part JPE described as an example in the sixth embodiment are not limited to the substantially rectangular shape or the substantially elliptical shape, and can include, for example, various shapes such as a substantially circular shape, a polygonal shape, or a substantially circular shape or elliptical shape having a groove portion.

Seventh Embodiment

Figure 11:
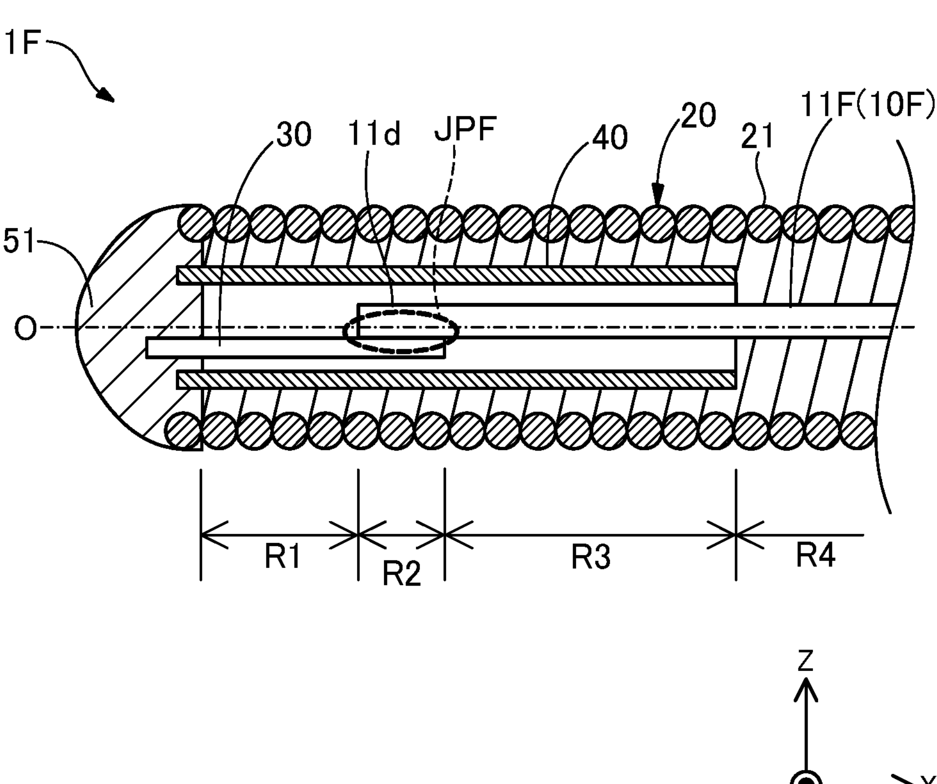
FIG. 11 is a partial sectional view illustrating a distal end side of a guide wire according to the seventh embodiment.

FIG. 11 is a partial sectional view illustrating a distal end side of a guide wire 1F according to the seventh embodiment. In the guide wire 1F according to the seventh embodiment, the first core shaft 10F includes a small-diameter portion 11F having a length in the axis line O direction (X-axis direction) longer than of the small-diameter portion 11 according to the first embodiment. The first core shaft 10F does not include the first decreasing-diameter portion 12, and the first large-diameter portion 15 (FIG. 1) is connected to a proximal end side of the small-diameter portion 11F. A joint part JPF between the first and second core shafts 10F and 30 is disposed on a distal end side of the small-diameter portion 11F. Incidentally, in the small-diameter portion 11F, only a part on the distal end side corresponding to the joint part JPF has a substantially rectangular transverse sectional shape illustrated in FIG. 3, and a part on the proximal end side of the joint part JPF has a transverse sectional shape other than the substantially rectangular shape (e.g. a substantially circular shape).

In the seventh embodiment as described above, a part where the first core shaft 10F (small-diameter portion 11F) on the proximal end side of the joint part JPF is covered by the covering portion 40 corresponds to the third region R3 (FIG. 11: third region R3). In addition, a part where the small-diameter portion 11F and the first large-diameter portion 15 of the first core shaft 10F are exposed from the covering portion 40 corresponds to the fourth region R4 (FIG. 11: fourth region R4). The guide wire 1D according to the seventh embodiment also accomplishes the same effect as in the first embodiment.

Eighth Embodiment

Figure 12:
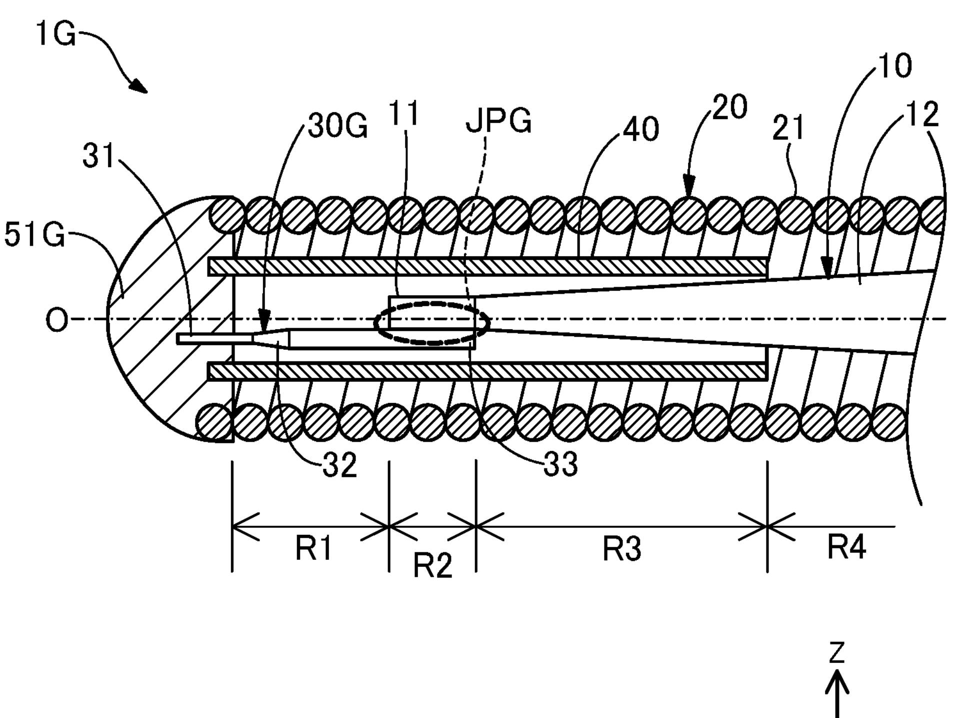
FIG. 12 is a partial sectional view illustrating a distal end side of a guide wire according to the eighth embodiment.

FIG. 12 is a partial sectional view illustrating a distal end side of a guide wire 1G according to the eighth embodiment. The guide wire 1G according to the eighth embodiment includes a second core shaft 30G having a different shape from the second core shaft 30 according to the first embodiment. The second core shaft 30G has a small-diameter portion 31, a decreasing-diameter portion 32, and a large-diameter portion 33 in this order from the distal end side to the proximal end side. An outer diameter and a length of each portion can be arbitrarily determined.

The small-diameter portion 31 is disposed on the distal end side of the second core shaft 30G, and has a substantially cylindrical shape with an outer diameter equivalent to the smallest outer diameter of the second core shaft 30G. The distal end side of the small-diameter portion 31 is fixed to the coil body 20 and the covering portion 40 by the distal end-side fixation portion 51G. The decreasing-diameter portion 32 is disposed between the small-diameter portion 31 and the large-diameter portion 33, and has a substantially truncated cone shape with an outer diameter decreasing from the proximal end side to the distal end side. The large-diameter portion 33 is disposed on the proximal end side of the second core shaft 30G, and has a substantially cylindrical shape with an outer diameter equivalent to the largest outer diameter of the second core shaft 30G. As illustrated in FIG. 12, the proximal end side of the large-diameter portion 33 is joined to the small-diameter portion 11 on the distal end side of the first core shaft 10. At least a part corresponding to a joint part JPG in the large-diameter portion 33 has a substantially elliptical transverse sectional shape with a major axis and a minor axis (as in FIG. 3).

Also in this guide wire 1G according to the eighth embodiment, the same effect as in the first embodiment can be accomplished. Additionally, in the guide wire 1G according to the eighth embodiment, the second core shaft 30G positioned in the first region R1 includes the decreasing-diameter portion 32 decreasing in diameter toward the distal end side and the small-diameter portion 31 having the smallest outer diameter, and therefore the distal end portion of the guide wire 1G can be more easily shaped. Incidentally, the configuration of the second core shaft 30G according to the eighth embodiment can be variously modified. For example, when a configuration including a flat portion 31 having a flat transverse sectional shape is adopted instead of the small-diameter portion 31, the flat portion 31 can be formed by pressing a distal end side of a substantially cylindrical material. Also, the transverse section of the large-diameter portion 33 can be formed into a substantially elliptical shape by presswork.

Ninth Embodiment

Figure 13:
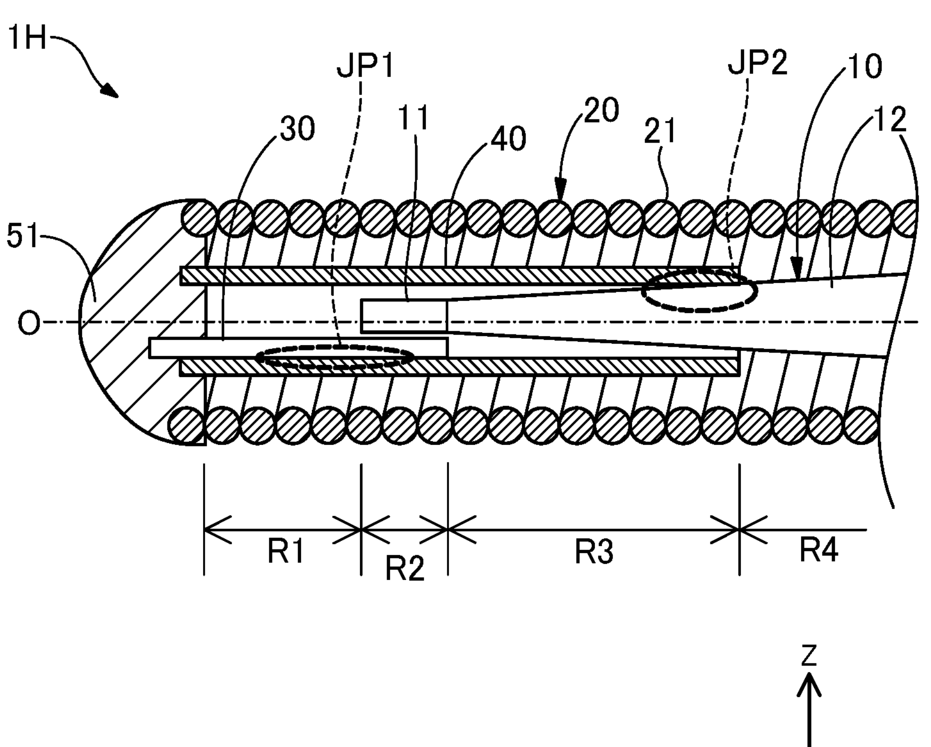
FIG. 13 is a partial sectional view illustrating a distal end side of a guide wire according to the ninth embodiment.

FIG. 13 is a partial sectional view illustrating a distal end side of a guide wire 1H according to the ninth embodiment. In the guide wire 1H according to the ninth embodiment, the first core shaft 10 and the second core shaft 30 are not directly joined to each other but are joined via the covering portion 40. Specifically, the outer side face of the second core shaft 30 and the inner side face of the covering portion 40 are joined to each other at least on a part in the axis line O direction to form a joint part JP1. In addition, the outer side face of the first core shaft 10 (first decreasing-diameter portion 12) and the inner side face of the covering portion 40 are joined to each other at least on a part in the axis line O direction to form a joint part JP2.

The covering portion 40 covers the first and second core shafts 10 and 30, and is fixed to the distal end-side fixation portion 51. Thus, the first core shaft 10 can be indirectly joined to the second core shaft 30 via the covering portion 40 by disposing the aforementioned joint part JP1 and joint part JP2. The guide wire 1H according to the ninth embodiment also accomplishes the same effect as in the first embodiment.

Tenth Embodiment

Figure 14:
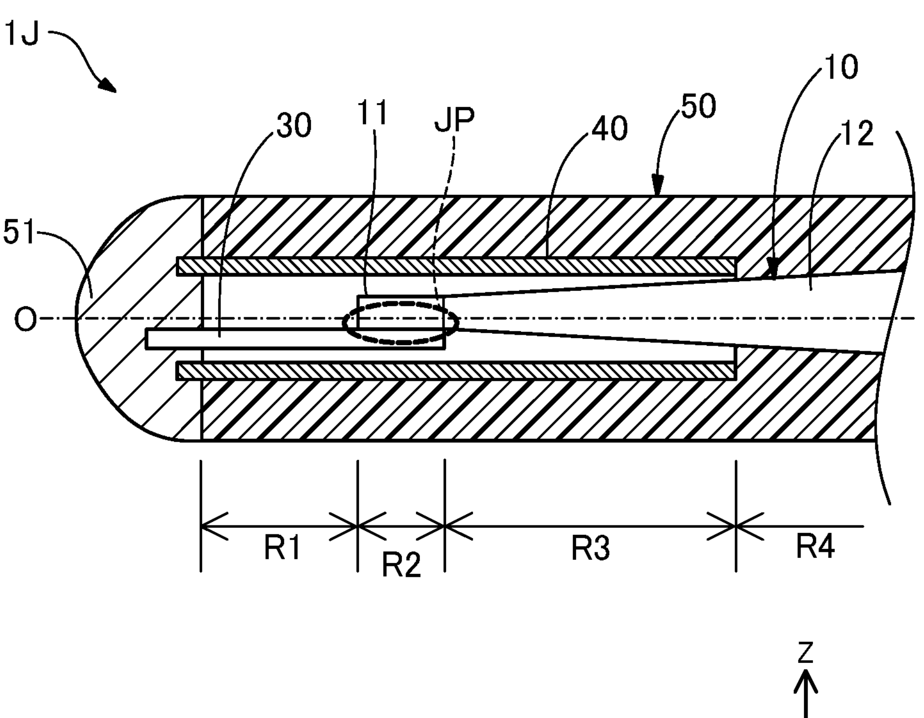
FIG. 14 is a partial sectional view illustrating a distal end side of a guide wire according to the tenth embodiment.

FIG. 14 is a partial sectional view illustrating a distal end side of a guide wire 1J according to the tenth embodiment. The guide wire 1J according to the tenth embodiment includes a resin body 50 instead of the coil body 20. The resin body 50 is arranged so as to cover the outside of the covering portion 40 and the first core shaft 10 not covered by the covering portion 40 (exposed from the covering portion 40). The guide wire 1J according to the tenth embodiment also accomplishes the same effect as in the first embodiment.

Modification Examples of the Embodiments

Note that the disclosed embodiments are not limited to the above embodiments, and can be implemented in various aspects without departing from the gist of the disclosed embodiments. For example, the following modifications are also possible.

Modification Example 1

In the aforementioned first to tenth embodiments, the configurations of the guide wire 1, 1A to 1J have been described as examples. However, the configuration of the guide wire can be variously changed. For example, the guide wire according to each of the embodiments has been explained as a medical appliance used for inserting a catheter into a blood vessel, but can be configured as a guide wire to be inserted into each organ in a human body, such as a lymphatic system, a biliary system, a urinary system, respiratory system, a digestive system, a secretory gland, and a genital organ. For example, the guide wire may be configured such that the second decreasing-diameter portion and the second large-diameter portion are absent, and the whole first core shaft is covered by the coil body. For example, the guide wire may be productized in a state that the distal end side is previously curved.

Modification Example 2

In the first to tenth embodiments, the configurations of the first and second core shafts 10, 10E, 10F, 30, 30E, and 30G have been described as examples. However, the configurations of the first and second core shafts can be variously modified. For example, the first core shaft may be configured so as not to have the first decreasing-diameter portion and the second decreasing-diameter portion and so as to have the same diameter throughout the axis line O. For example, in the joint part JP (FIG. 3), the arrangements of the first and second core shafts in the Z-axis direction may be reversed. Also, on the joint part JP (FIG. 3), the first and second core shafts may be adjacent to each other in the Y-axis direction. For example, the first core shaft may be composed of a plurality of core shaft members that are joined together. In this case, each core shaft member may be made of the same material or different materials.

Modification Example 3

In the first to tenth embodiments, the configuration of the coil body 20 has been described as an example. However, the configuration of the coil body can be variously changed. For example, the coil body may have a densely-wound structure without gaps between the adjacent wires, a coarsely-wound structure with gaps between the adjacent wires, or a mixed structure of the densely-wound structure and the coarsely-wound structure. In addition, the coil body may include a resin layer coated with e.g. a hydrophobic resin material, a hydrophilic resin material, or a mixture thereof. For example, a transverse sectional shape of the wire of the coil body is not necessarily the substantially circle shape.

Modification Example 4

The configurations of the guide wires 1, 1A to 1J according to the first to tenth embodiments, and the configurations of the guide wires according to the modification examples 1 to 3 may be appropriately combined. For example, in the guide wire 1A according to the second embodiment (configuration in which the joint part JPA is disposed on the first decreasing-diameter portion), the transverse sectional shapes of the first core shaft (first decreasing-diameter portion) and second core shaft corresponding to the joint part may be different from each other. In addition, for the guide wire 1A according to the second embodiment, it is possible to adopt the configuration including the distal end region (the third embodiment), the configuration without the third region (the fourth embodiment), the configuration without the fourth region (the fifth embodiment), or the configuration including the resin body instead of the coil body (the tenth embodiment). In addition, for the guide wire 1H according to the ninth embodiment (configuration in which the first and second core shaft are indirectly joined to each other), it is possible to adopt the configuration including the distal end region (the third embodiment), the configuration without the third region (the fourth embodiment), the configuration without the fourth region (the fifth embodiment), or the configuration including the resin body instead of the coil body (the tenth embodiment).

As described above, the present aspects have been explained based on the embodiments and the modification examples, and the embodiments of the aforementioned aspects are intended to facilitate understanding of the present aspects and not to limit the present aspects. The present aspects can be modified and improved without departing from the gist of the aspects and claims, and the present aspects include equivalents thereof. In addition, if technical characteristics of the present aspects are not explained as essentials in this specification, the technical characteristics can be appropriately deleted.

What is claimed is:

1. A guide wire comprising:
- a first core shaft made of a superelastic material and having a small-diameter portion, a decreasing-diameter portion in which an outer diameter of the first core shaft decreases in a distal direction, and a large-diameter portion, in this order from a distal end side of the first core shaft to a proximal end side of the first core shaft;
- a second core shaft made of a material more susceptible to plastic deformation than the superelastic material of the first core shaft and having a proximal end side laterally joined to the small-diameter portion of the first core shaft;
- a covering portion covering (i) a joint part between the first core shaft and the second core shaft and (ii) at least a part of the second core shaft that is on a distal end side of the joint part;
- a distal end-side fixation portion fixed to a distal end portion of the second core shaft and a distal end portion of the covering portion; and
- a coil body covering the second core shaft and the covering portion, wherein:
- the guide wire includes, from a distal end side of the guide wire toward a proximal end side of the guide wire:
  - a first region where the second core shaft on a distal end side of the joint part is covered by the covering portion, and
  - a second region adjacent to the first region, where the joint part is covered by the covering portion,
- the first region is more susceptible to plastic deformation than the second region;
- the covering portion is configured to be less susceptible to plastic deformation than the second core shaft and more susceptible to plastic deformation than the first core shaft, and the distal end portion of the covering portion is fixed to the second core shaft by the distal end-side fixation portion, and a proximal end portion of the covering portion is not fixed to the first core shaft.

2. The guide wire according to claim 1, further including:

a distal end region disposed on a distal end side of the first region, and where the second core shaft is exposed from the covering portion, wherein the distal end region is more susceptible to plastic deformation than the first region.

3. The guide wire according to claim 1, further including:

a third region disposed on a proximal end side of the second region, and where the first core shaft is covered by the covering portion, wherein:

the covering portion further covers at least a part of the first core shaft that is on a proximal end side of the joint part, and the third region is less susceptible to plastic deformation than the second region.

4. The guide wire according to claim 3, further including:

a fourth region disposed on a proximal end side of the third region, and where the first core shaft is exposed from the covering portion, wherein the fourth region is less susceptible to plastic deformation than the third region.

5. The guide wire according to claim 1, wherein:

in the joint part, a transverse sectional shape of the first core shaft is different from a transverse sectional shape of the second core shaft.

6. The guide wire according to claim 1, wherein:

the first core shaft in the joint part has a substantially rectangular transverse sectional shape, and the second core shaft in the joint part has a substantially elliptical transverse sectional shape.

7. The guide wire according to claim 1, wherein the joint part is disposed at the decreasing-diameter portion.

8. The guide wire according to claim 2, further including:

a third region disposed on a proximal end side of the second region, and where the first core shaft is covered by the covering portion, wherein:

the covering portion further covers at least a part of the first core shaft that is on a proximal end side of the joint part, and the third region is less susceptible to plastic deformation than the second region.

9. The guide wire according to claim 8, further including:

a fourth region disposed on a proximal end side of the third region, and where the first core shaft is exposed from the covering portion, wherein the fourth region is less susceptible to plastic deformation than the third region.

10. The guide wire according to claim 2, wherein:

in the joint part, a transverse sectional shape of the first core shaft is different from a transverse sectional shape of the second core shaft.

11. The guide wire according to claim 2, wherein:

the first core shaft in the joint part has a substantially rectangular transverse sectional shape, and the second core shaft in the joint part has a substantially elliptical transverse sectional shape.

12. The guide wire according to claim 2, wherein the joint part is disposed at the decreasing-diameter portion.

13. The guide wire according to claim 3, wherein:

in the joint part, a transverse sectional shape of the first core shaft is different from a transverse sectional shape of the second core shaft.

14. The guide wire according to claim 1, wherein a proximal end of the covering portion is located in a middle region of the decreasing-diameter portion.

15. A guide wire comprising:

a first core shaft made of a superelastic material and having a small-diameter portion, a decreasing-diameter portion in which an outer diameter of the first core shaft decreases in a distal direction, and a large-diameter portion, in this order from a distal end side of the first core shaft to a proximal end side of the first core shaft;

a second core shaft made of a material more susceptible to plastic deformation than the superelastic material of the first core shaft and having a proximal end side laterally joined to the small-diameter portion of the first core shaft;

a covering portion covering (i) a joint part between the first core shaft and the second core shaft and (ii) at least a part of the second core shaft that is on a distal end side of the joint part;

a distal end-side fixation portion fixed to a distal end portion of the second core shaft and a distal end portion of the covering portion; and a coil body covering the second core shaft and the covering portion, wherein:

the guide wire includes, from a distal end side of the guide wire toward a proximal end side of the guide wire:

a first region where the second core shaft on a distal end side of the joint part is covered by the covering portion, and a second region adjacent to the first region, where the joint part is covered by the covering portion, the first region is more susceptible to plastic deformation than the second region;

in each section where the coil body covers the covering portion, the coil body contacts only the distal end-side fixation portion, and the distal end portion of the covering portion is fixed to the second core shaft by the distal end-side fixation portion, and a proximal end portion of the covering portion is not fixed to the first core shaft.

16. A guide wire comprising:

a core shaft having a first core shaft and a second core shaft;

the first core shaft having a small-diameter portion, a decreasing-diameter portion in which an outer diameter of the first core shaft decreases in a distal direction, and a large-diameter portion, in this order from a distal end side of the first core shaft to a proximal end side of the first core shaft;

a joint part that contacts a distal end of the first core shaft and a proximal end of the second core shaft;

a covering portion covering (i) the joint part and (ii) at least a part of the second core shaft that is on a distal end side of the joint part;

a distal end-side fixation portion fixed to a distal end portion of the second core shaft and a distal end portion of the covering portion; and a coil body covering the second core shaft and the covering portion, wherein the guide wire includes, from a distal end side of the guide wire toward a proximal end side of the guide wire:

a first region where the second core shaft on the distal end side of the joint part is covered by the covering portion, and a second region adjacent to the first region, where the joint part is covered by the covering portion, in each section where the coil body covers the covering portion, the coil body contacts only the distal end-side fixation portion, and the distal end portion of the covering portion is fixed to the second core shaft by the distal end-side fixation portion, and a proximal end portion of the covering portion is not fixed to the first core shaft.

17. The guide wire according to claim 16, wherein the second core shaft has a proximal end side laterally joined to the small-diameter portion of the first core shaft.

18. The guide wire according to claim 16, wherein the first region is more susceptible to plastic deformation than the second region.

19. The guide wire according to claim 16, wherein the outer diameter of the distal end-side fixation portion is greater than the outer diameter of the covering portion.

20. The guide wire according to claim 16, wherein a maximum outer diameter of the second core shaft is greater than the outer diameter of the covering portion.

21. The guide wire according to claim 16, wherein the proximal end portion of the covering portion is not fixed.

* * * * *